United States Patent [19]

Tesic et al.

[11] Patent Number: 5,287,546
[45] Date of Patent: Feb. 15, 1994

[54] PATIENT POSITIONING APPARATUS FOR BONE SCANNING

[75] Inventors: Mike M. Tesic, Verona; Richard B. Mazess, Madison; James A. Hanson, Madison; James G. Deluhery, Madison, all of Wis.

[73] Assignee: Lunar Corporation, Madison, Wis.

[21] Appl. No.: 976,797

[22] Filed: Nov. 16, 1992

Related U.S. Application Data

[63] Continuation-in-part of Ser. No. 944,626, Sep. 14, 1992, Pat. No. 5,228,068.

[51] Int. Cl.$^5$ .............................................. A61B 6/00
[52] U.S. Cl. ...................................... 378/54; 378/55; 128/653.1
[58] Field of Search ................. 378/54, 55, 56, 57, 378/8, 95; 128/653.1

[56] References Cited

U.S. PATENT DOCUMENTS

| | | | |
|---|---|---|---|
| 2,818,510 | 12/1957 | Verse | 250/91 |
| 3,617,749 | 11/1971 | Masslot | 250/92 |
| 3,670,163 | 6/1982 | Lajus | 250/57 |
| 3,892,967 | 7/1975 | Grady et al. | 250/447 |
| 4,024,403 | 5/1977 | Bernstein et al. | 250/445 |
| 4,150,297 | 4/1979 | Borggren | 250/490 |
| 4,210,815 | 7/1980 | Riehl | 250/445 |
| 4,293,770 | 10/1981 | Vavrek | 250/445 |
| 4,298,801 | 11/1981 | Heitman et al. | 250/447 |
| 4,358,856 | 11/1982 | Stivender et al. | 250/468 |
| 4,363,128 | 12/1982 | Grady et al. | 378/181 |
| 4,365,343 | 12/1982 | Grady et al. | 378/181 |
| 4,501,011 | 2/1985 | Hauck et al. | 378/196 |
| 4,541,293 | 9/1985 | Caugant et al. | 74/89.18 |
| 4,635,284 | 1/1987 | Christiansen | 378/197 |
| 4,653,083 | 3/1987 | Rossi | 378/196 |
| 4,716,581 | 12/1987 | Barud | 378/198 |
| 4,756,016 | 7/1988 | Grady et al. | 378/197 |
| 4,903,203 | 2/1990 | Yamashita et al. | 378/54 X |
| 4,986,273 | 1/1991 | O'Neill et al. | 378/55 X |
| 4,987,585 | 1/1991 | Kidd et al. | 378/197 |
| 5,014,292 | 5/1991 | Siczek et al. | 378/196 |
| 5,165,410 | 11/1992 | Warne et al. | 378/55 X |
| 5,172,695 | 12/1992 | Cann et al. | 328/54 X |

FOREIGN PATENT DOCUMENTS

3542333 11/1985 Fed. Rep. of Germany .
56-155937 12/1981 Japan .

OTHER PUBLICATIONS

Polystar, "Dedicated Interventional X-Ray System With Tilt Table and Integrated C-Arm", Federal Republic of Germany no date.
Philips Medical Systems, "Integris 12000 for Interventional Radiology". No date.

Primary Examiner—David P. Porta
Attorney, Agent, or Firm—Quarles & Brady

[57] ABSTRACT

A desitometer gantry may translate in two directions for scanning and may swivel about a vertical axis to allow the radiation angle and the detector-to-patient distance to be altered during a scan so as to provide constant magnification of the image and to align the patient's spine with the radiation beam for more accurate edge measurements. A method of reducing the effects of osteophytes on density measurements applies an iterative threshold based on the density difference between hard and soft tissue.

5 Claims, 7 Drawing Sheets

FIG. 3(a)
FIG. 3(b)
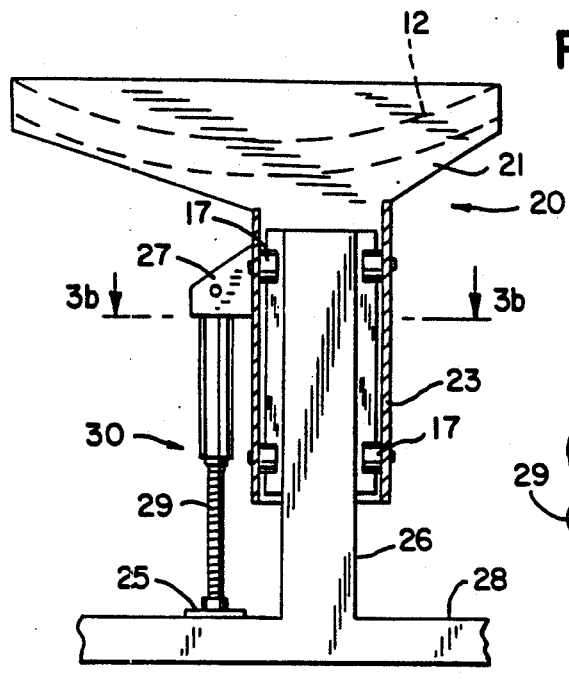
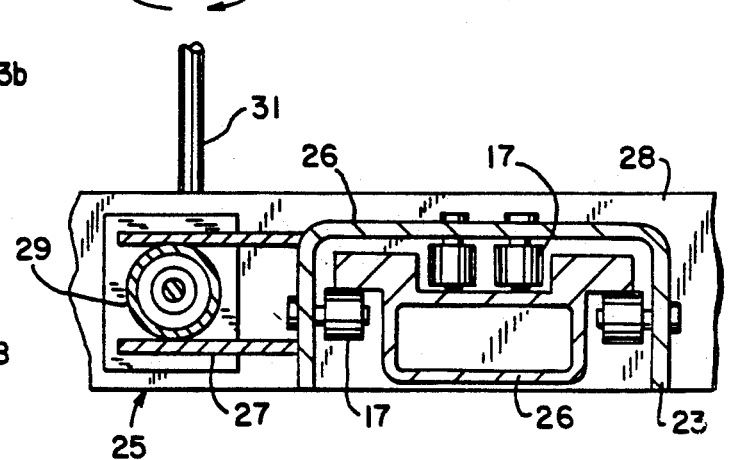
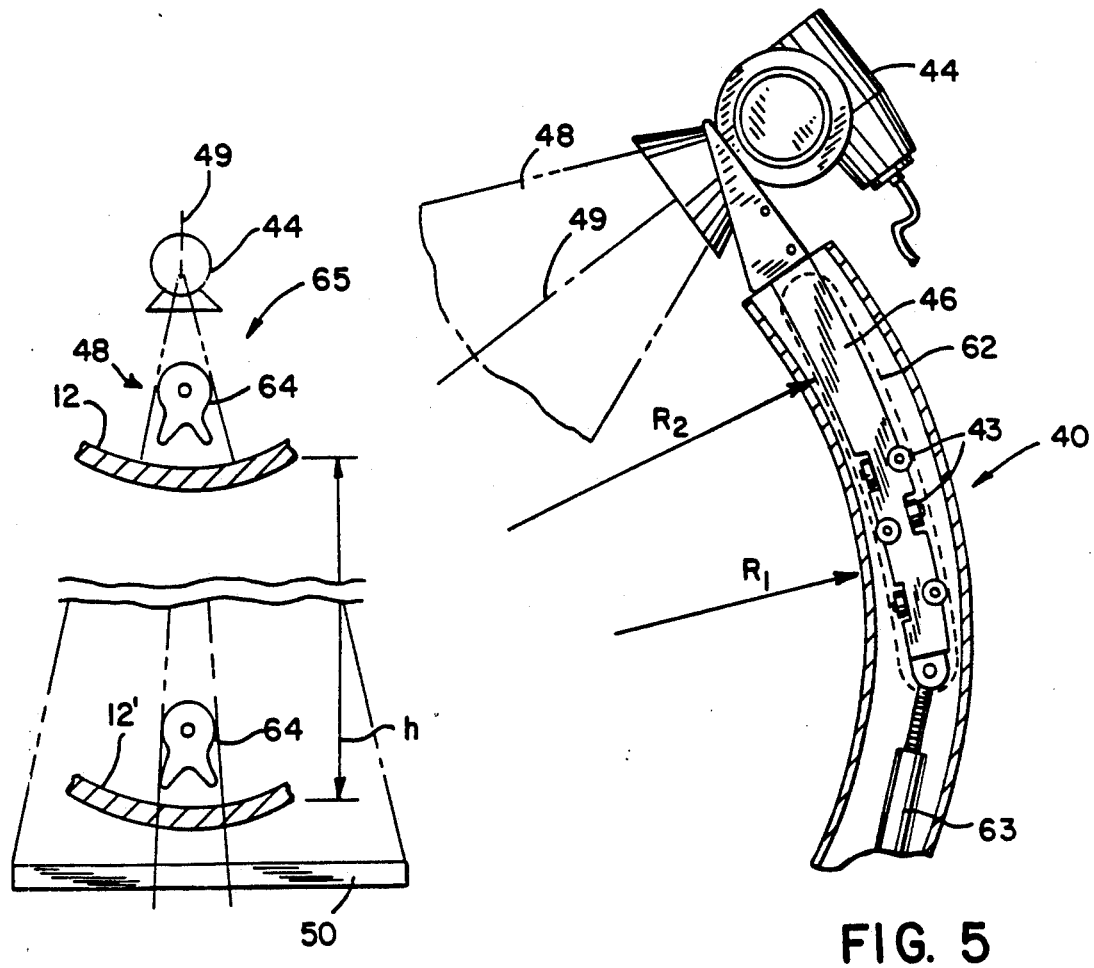
FIG. 4
FIG. 5

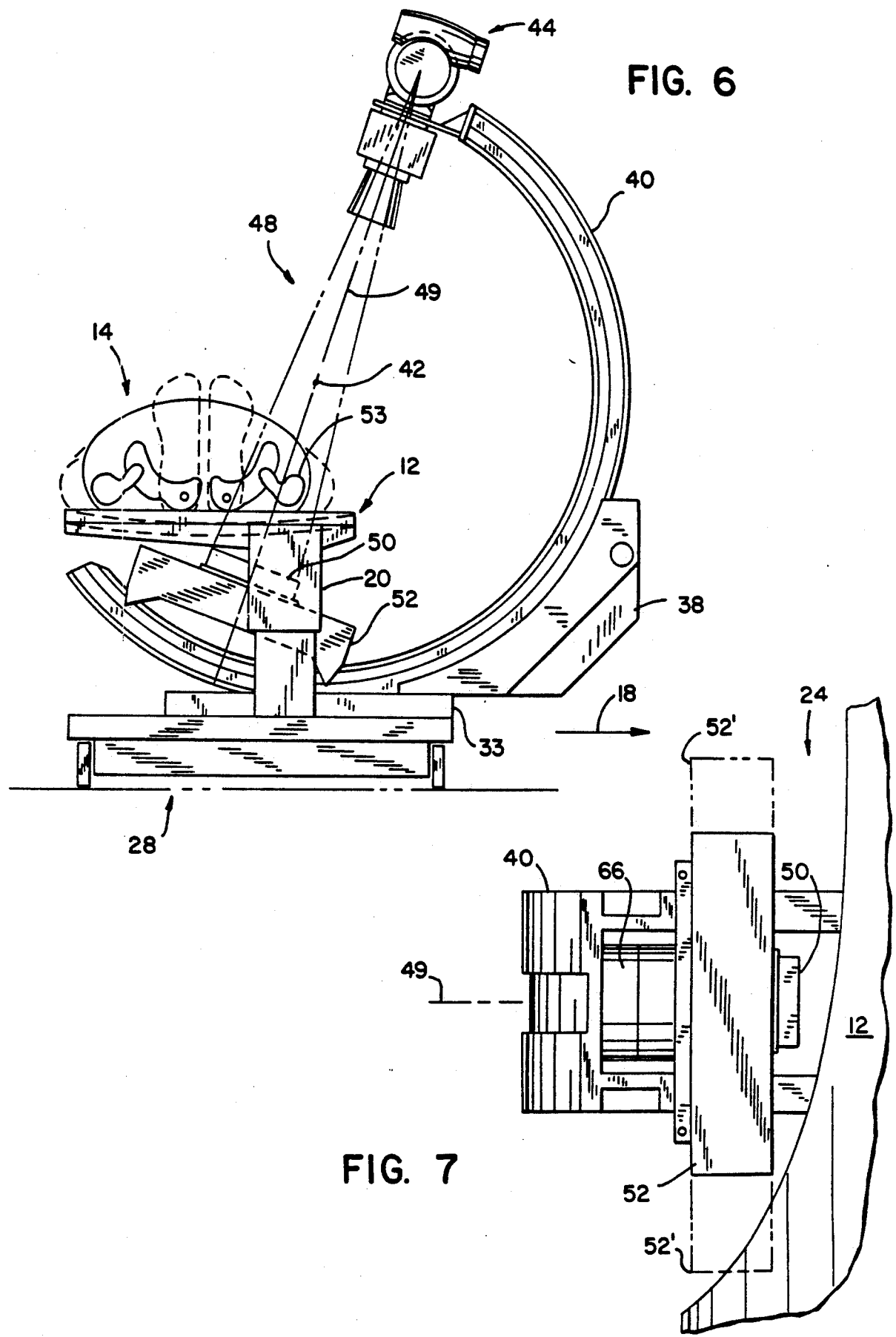

PATIENT POSITIONING APPARATUS FOR BONE SCANNING

This application is a continuation-in-part of application Ser. No. 07/944,626 filed Sep. 14, 1992, and entitled: "Method for Analyzing Vertebral Morphology Using Digital Radiography" now U.S. Pat. No. 5,228,068.

FIELD OF THE INVENTION

The present invention relates generally to radiographic instruments and more particularly to an apparatus for positioning and scanning a patient for evaluation of bone density and bone morphology.

BACKGROUND OF THE INVENTION

Scanning radiographic equipment differs from conventional radiography in that it employs a narrowly collimated beam of radiation, typically x-rays formed into a fan or pencil beam, rather than a broad area cone beam. The small beam size used in scanning radiographic equipment allows replacement of an image forming sheet of radiographic film, used with conventional radiographic equipment, with a small area electronic detector element or array of such elements.

The detector elements receiving the transmitted radiation produce electrical signals which may be converted to digital values by an analog to digital converter for the later development of an image or for other processing by computer equipment. The ability to quantify the measurement of the transmitted radiation, implicit in the digitization by the analog to digital converter, allows not only the formation of a radiographic "attenuation" image but also the mathematical analysis of the composition of the attenuating material by dual energy techniques. See generally, "Generalized Image Combinations in Dual KVP Digital Radiography", by Lehmann et al Med Phys 8(5) Sep./Oct. 1981.

Such dual energy techniques quantitatively compare the attenuation of radiation at two energies to distinguish, for example, between bone and soft tissue. Dual energy techniques allow the measure of bone mass, such measurement being important in the treatment of osteoporosis and other bone diseases.

The limited area of the beam of radiation used in scanning radiographic systems requires that the beam be moved over an area, if a conventional image is to be formed. Typically, the pencil or fan beam will be scanned in a raster pattern over the area to be measured, each line of the scan separated by the width of the pencil or fan beam, with the directions of scanning being generally perpendicular to the direction of the radiation.

Images formed by a scanning radiographic system are potentially more accurate than those produced by a typical broad beam radiograph system. This accuracy arises from the limited divergence of the rays of the pencil or fan beam from the principal axis of the radiation, as compared to a broad area cone beam. This narrow collimation of the pencil or fan beam reduces "parallax" in the projected image, potentially providing extremely accurate morphological measurements of certain structures such as the vertebrae in the spine. Such morphological measurements are used to evaluate various dimensions of a vertebra to detect crushing or other deformation that are one element of certain bone diseases such as osteoporosis. See e.g. Minne et al., "A Newly Developed Spine Deformity Index (SDI) to Quantitate Vertebral Crush Factors in Patients with Osteoporosis," *Bone and Mineral*, 3:335–349 (1988); J. C. Gallagher et al, "Vertebral Morphometry: Normative Data," *Bone and Mineral*, 4:189–196 (1988); Hedlund et al, "Vertebral Morphometry in Diagnosis of Spinal Fractures," *Bone and Mineral*, 5:59–67 (1988); and Hedlund et al, "Change in Vertebral Shape in Spinal Osteoporosis," *Calcified Tissue International*, 44:168–172 (1989). Automatic techniques for morphological measurements of bone are described in U.S. patent application Ser. No. 07/944,626 filed Sep. 14, 1992 and entitled: "Method for Analyzing Vertebral Morphology Using Digital Radiography" assigned to the same assignee as the present application and hereby incorporated by reference In order to make accurate morphological measurements and to provide clinically valuable dual energy measurements of a variety of body structures, the radiation source and detector should be easily positioned at different angles about the patient. Further, at each such angle, the radiation source and detector must have the necessary clearance from the patient to perform the required scanning. Because the scanning can take some length of time, the patient must be fully supported, typically in a supine position, and yet ideally the patient support must be constructed so as to not unduly interfere with the attenuation measurements made during the scan. Finally, the positioning of the patient with respect to the radiation source and detector should be such as to maximize the quality of the morphological data obtained.

SUMMARY OF THE INVENTION

The present invention provides a table and gantry system, the latter for holding a radiation source and detector, which together cooperate to produce a compact and flexible scanning radiographic system. The table and gantry cooperate to allow one to obtain quality morphological data, by scanning, at a wide range of angles about the patient with minimum interference from the table.

The densitometer includes a table for holding a supine patient in a horizontal plane. A track permits movement of a pallet with respect to the table along a first and second perpendicular axis parallel to the horizontal plane and a collar attached to the pallet holds a C-arm that may slide thorough the collar. The C-arm has a radiation source and detector affixed to its ends to be in opposition about an center and may rotate the radiation source and detector to one of a plurality of angles about an axis parallel to the horizontal plane. At each such angle a dual energy attenuation measurements may be made along a beam axis extending between the radiation source and detector. In one embodiment, the table includes a support for moving the table in a vertical direction with respect to the track.

It is one object of the invention to provide a densitometer that may scan a patient at dual energies along an arbitrary angle as controlled by the position of the C-arm. The motion of the pallet and table provide three degrees of translational freedom which allow the C-arm to scan in an arbitrary plane. This flexibility allows scanned images of specific structures, such as the femur, to be obtained from a desired angle without repositioning the patient.

The radiation source may produce a fan beam of rays of radiation diverging along a fan beam plane and the detector may be a linear array of detector elements, each element measuring the intensity of radiation along one ray of the fan beam. The fan beam and detector array may be mounted to the C-arm so that the fan beam and the detector array may rotate about a fan beam axis connecting the radiation source and the detector array.

It is thus another object of the invention to allow the scanning of the patient along an arbitrary angle as positioned by the C-arm, wherein one axis of scanning is obtained by the electrical scanning of the detector elements of the linear array.

It is another object of the invention to allow for the minimization of parallax in anterior/posterior scans of the patient, such scan which may be used for morphological measurements. The ability to reposition the table downward permits the patient to be moved as close as possible to the detector array thus reducing the divergence of the radiation beams received by the detector and the parallax of the generated image. The patient table may be raised to allow rotation of the gantry to other positions and to reduce the patient's effort in getting on and off of the table. The ability to move the table upward during motion of the gantry to avoid interference with the gantry permits the size of the gantry to be reduced allowing for a more compact imaging system.

As mentioned, the gantry holds a radiation source that may direct a planar fan beam of radiation toward an opposed detector positioned on the gantry. Both the radiation source and the detector are rotatable about a line between the two so that the scanning direction may be changed with the orientation of the fan beam adjusted so that the direction of scanning remains perpendicular to the fan beam plane. The ability to adjust the direction of scanning reduces the effect of patient motion on the resultant data by allowing the selection of a scanning pattern where adjacent points in space are scanned at proximate times.

The detector array for the fan beam may be rotated independently of the radiation source so as to reduce its swept volume during motion of the gantry.

It is therefore another object of the invention to allow the size of the gantry to be reduced without causing collisions between the detector array and the table. Rotation of the detector array to its orientation of least swept volume allows the detector array to pass through the reduced width area of the table during movement of the gantry to a new position without translation of the gantry.

In one embodiment, the gantry may be a C-arm held slidably in a collar so that its first and second end rotate about an isocenter. A support beam having a mounting end may be attached to the first end of the C-arm with a sleeve so that it may slide away from the first end to a plurality of distances. Either the radiation source or detector may be attached to the mounting end of the support beam. In addition, the other of the source or detector may be attached to a carriage that slides on the inner radius of the C-arm in from the second end.

It is a further object of the invention to provide the greatest possible freedom in angular orientation of the detector and source about a patient while using a C-arm type structure. The sliding support beam and carriage provide an effective increase in angular positioning range beyond that which can normally be obtained by the geometry of the C-arm.

The source and detector may be positioned at two substantially perpendicular angles and a scan of the patient obtained at these angles to produce a first and second array of pixels, each pixel representing bone mass at a corresponding location in the patient. The pixel array at the first angle is analyzed to determine a plurality of center of bone mass values at points along an axis of the pixel array corresponding to a principle scanning direction. During the scanning of the patient at the second angle along this principle scanning direction, the position of the detector with respect to the patient is adjusted in accordance with the determined center of bone mass values. The detector may be adjusted to maintain an essentially constant distance with respect to the center of mass of the patient, indicated by the center of mass values, and hence a constant magnification of the spine. Or the angle of the radiation received by the detector may be adjusted to remain substantially perpendicular to the spine at the point of imaging.

It is thus another object of the invention to employ two scans at different angles with the first scan being used to correct the second scan which may then be used for morphological measurements. Adjustment of positioning of the detector during the second scan allows the fidelity of the generated image to be improved for dimension measuring purposes.

A histogram of selected pixels acquired during the scan may be reviewed to compile a multiple-mode density histogram providing number of pixels as a function of pixel density value. From this histogram, a soft tissue average and hard tissue average may be determined corresponding to average density values of soft and hard tissue, such as bone, respectively. A threshold above the hard tissue average based on the difference between the hard tissue average and the soft tissue average is generated and the hard tissue average is recomputed ignoring pixels above the threshold. This process is repeated until the change in the computed hard tissue average is below a predetermined threshold and that hard tissue average is designated as the density of the region of interest.

It is thus another object of the invention to remove the effects of osteophytes, i.e., bone elements having density harder than normal bone, from the calculation of bone density and other bone measurements. The closeness of the osteophytes to the density values of normal bone renders simple thresholding techniques inaccurate.

The table includes a first and second upwardly extending pillar separated by a distance greater than the height of the patient. A horizontal support surface stretches between the top ends of the pillars to span that distance without additional support. The width of the table narrows towards the table center. In one embodiment, the horizontal support surface may be concave upward to provide increased rigidity to the horizontal support surface area.

It is one object of the invention to provide a sturdy patient support that does not interfere with the scanning process both with respect to the motion of the gantry and with respect to undesired attenuation of the radiation beam. The design of the table removes support structures from the imaging area and allows the support surface to be relatively thin. A reduction of the width of the table near the center, and thus near an important area for imaging, reduces the attenuation of the radiation caused by the table for lateral scans often used for collecting attenuation sensitive bone density information. The greater width of the table near its ends offers a comforting larger supporting width near the patient's head and feet; the reduced width at the center makes it easier for the patient to get on and off the table. In the embodiment with the concave upward surface, the table's narrowing reduces the height of its lip at the center further improving patient access.

The foregoing and other objects and advantages of the invention will appear from the following description. In the description reference is made to the accompanying drawings which form a part hereof and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 3(a) is a cross-section of one support for the table of FIG. 1 taken along line 3(a)—3(a) in FIG. 1 showing the upward curvature of the table surface and the mechanism for elevating and lowering the table;

FIG. 3(b) is a cross-section of the support of FIG. 3(a) taken along line 3(b)—3(b) of FIG. 3(a);

FIG. 4 is an exaggerated depiction of the table in conjunction with a radiation source and detector showing the effect of table height on the divergence of the rays of the illuminating radiation as is related to problems of parallax;

FIG. 5 is a cross section of the gantry taken along lines 5—5 of FIG. 1 showing an internal sleeve and support beam for holding the radiation source at a variety of distances from the end of the gantry C-arm and the different radiuses of motion produced by motion of the C-arm and motion of the sliding support beam;

FIG. 6 is a view in elevation of the densitometer of FIG. 1 taken along the longitudinal axis showing displacement of the center of rotation of the C-arm and the rotation of the C-arm for proper imaging of a femur of the patient without inward rotation of the patient's leg;

FIG. 7 is a plan view of a detail of the table of FIG. 1 showing interference between the table and the detector array when the detector array is in a first position, in phantom, and clearance when the detector array is in the second position;

DETAILED DESCRIPTION OF THE PREFERRED EMBODIMENT

Figure 1:
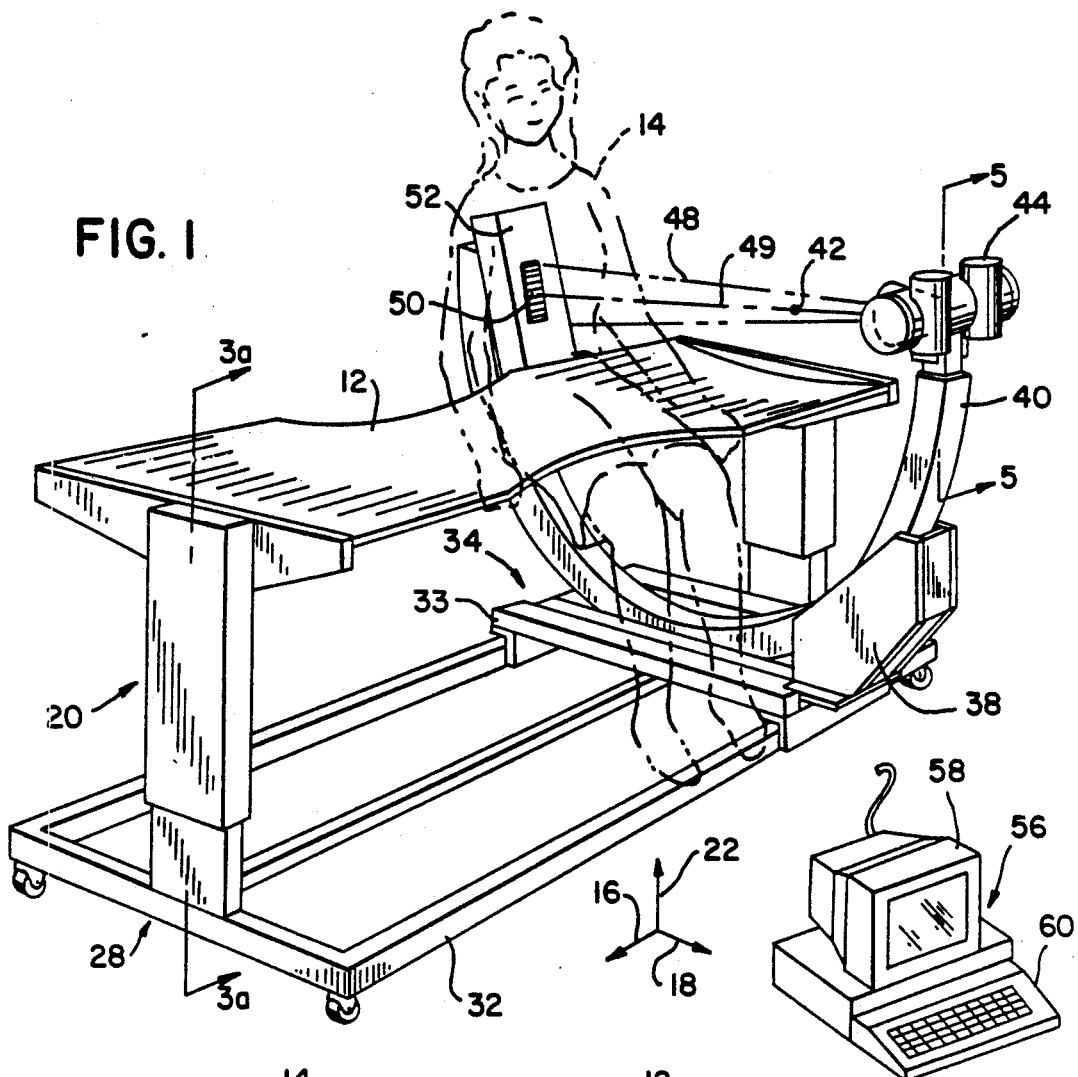
FIG. 1 is a perspective view of the present invention showing a C-arm, having an x-ray source and a detector, and a table positioned for mounting by the patient and a controlling computer.

Referring to FIG. 1, a bone densitometer 10 constructed according to the present invention includes a table 12 for supporting a patient 14 in a sitting position prior to or after an examination (as shown) or in a supine position along the table's longitudinal axis 16 during an examination. The table 12 is constructed of epoxy impregnated carbon fiber laminated over a foamed plastic core. This combination of materials is extremely light, and thus generally radiolucent, and stiff. Further, the attenuation is extremely uniform so as to prevent the introduction of artifacts into the radiographic images. The table 12 has a generally linear cross-section along the longitudinal axis 16 and an upwardly concave cross-section along a transverse axis 18 perpendicular to the longitudinal axis 16. Thus, the table 12 is a trough-shaped sheet whose transverse curvature provides additional resistance to longitudinal bending.

Support pillars 20 hold either longitudinal end of the table 12. The support pillars 20 are separated by a distance greater than the typical height of the patients to be examined so that the support pillars 20 do not obstruct the scanning process nor attenuate the measuring radiation. The longitudinal stiffness of the table 12 allows it to bridge the distance between the pillars 20 as an unsupported horizontal span thereby eliminating additional radiation attenuating structure.

Figure 2A:
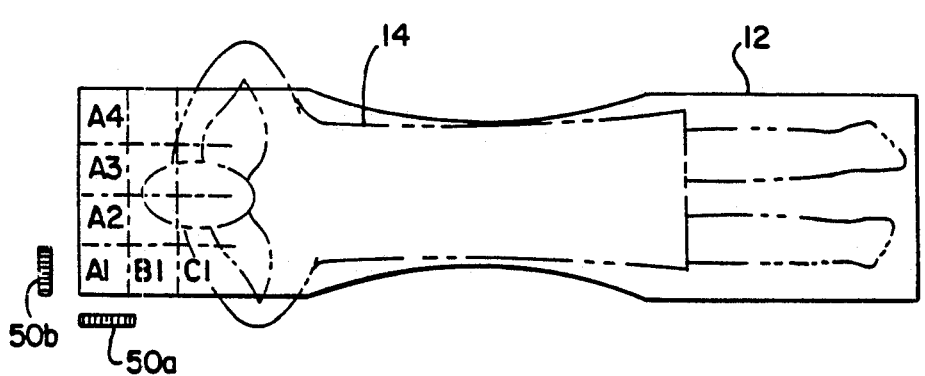
FIGS. 2(a) and 2(b) are plan and elevation views of the table of FIG. 1 showing the hourglass shape of the table and two possible scanning patterns that may be employed by the present invention.
Figure 2B:
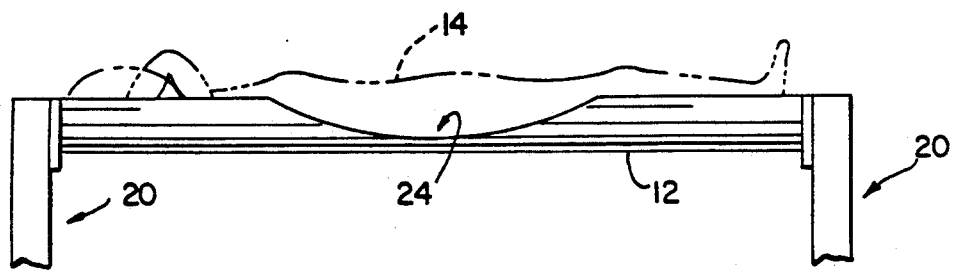
Figure 9:
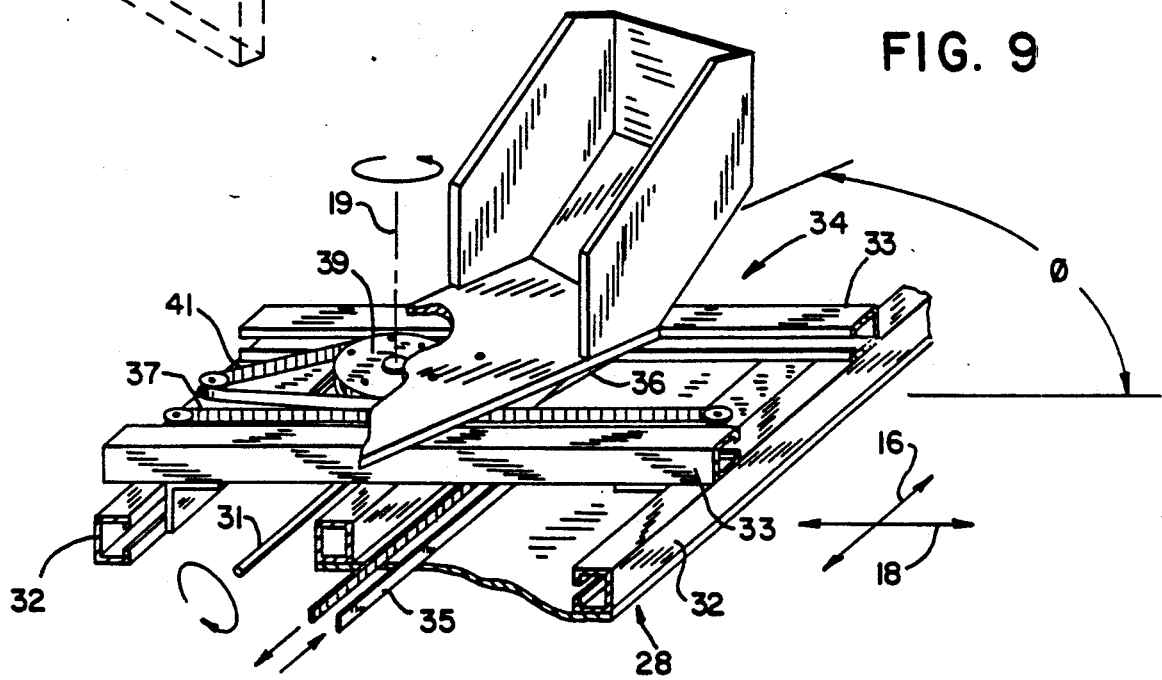
FIG. 9 is a perspective cutaway view of the supporting mechanism for the C-arm of FIG. 1 showing rotation of the C-arm with respect to the gantry pallet and the x and y translation of the pallet.

In one embodiment shown in FIG. 2(b) the transverse width of the table 12 varies along its longitudinal extent being widest near the support pillars 20, and thus near the head and feet of the patient 14 when the patient 14 is in the supine position on the table 12, and narrowest at the mid-portion of the table 12 corresponding generally to the area of the patient's vertebrae when the patient is in the supine position. This narrowing of the table 12 is in the form of two rounded notches 24 extending inward toward the center of the table from either transverse edge and imparting to the table an hourglass shape as viewed along a vertical axis 22 perpendicular to the longitudinal and transverse axes 16 and 18 respectively Referring now to FIGS. 1, 3(a) and 3(b), support pillars 20 extend vertically downward around upward extending posts 26, the latter which are attached, at their bottom ends, to a bed 28 supporting the densitometer 10. The support pillars 20 each include a horizontal architrave 21, extending the width of the table 12 and attached to a respective end of the table 12, and vertical channel shaped casing 23 surrounding the posts 26 to vertically slide in engagement with the posts 26 guided by a set of rollers 17 attached to the casing 23. The casings 23, and hence the support pillars 20, may be positioned vertically as driven by actuators 30 each comprising a nut 27 attached to an outer casing wall and a lead screw 29 received at one end by the nut 27 and at the other end by a right angled drive 25 attached beneath the nut to the bed 28. A common drive shaft 31 connects each right angled drive 25 to a single stepper motor (not shown) so that rotation of the drive shaft 31 turns the right angled drives 25 and hence the lead screws 29 in tandem so as to raise and lower the table 12 on pillars 20 while maintaining the table's horizontal attitude The number of steps made by the stepper motor is simply related to the change in table height Referring to FIGS. 1 and 9, the bed 28 includes two longitudinal rails 32 which form a track for supporting a transversely extending gantry pallet 34, and which allow the gantry pallet 34 to be positioned longitudinally along substantially the entire length of the densitometer 10 (as indicated by longitudinal axis 16).

The gantry pallet 34 includes transverse rails 33 carried by rollers (not visible) fitting within the rails 32 and motivated by a stepper motor driven flexible belt 35. Riding on the rails 33 of the gantry pallet 34 is a slider 36 moved transversely by stepper motor driven belt 37. The slider 36 supports a turntable 39 having a vertically oriented axis of rotation 19 and rotated by mean of stepper motor driven belt 41. As before, the stepper motors driving belts 35, 37 and 41 allow a determination of the precise movement of their respective components through a tallying of the steps taken, as will be understood to those of ordinary skill in the art.

The turntable 39 supports a C-arm collar 38. Collar 38 is generally arcuate to enclose and slidably hold a C-arm 40 such that the ends of the C-arm may rotate about an isocenter 42 as the body of the C-arm 40 slides through the collar 38. The C-arm 40 is constructed as described in U.S. Pat. No. 4,955,046 to Aldona A. Siczek and Bernard W. Siczek entitled: "C-Arm for X-ray Diagnostic Examination". The C-arm 40 is motorized, as is understood in the art, to allow remote control over the positioning of the C-arm 40 in collar 38. The radiation source 44, which includes an x-ray tube together with filter and collimator as will be described in detail below, is mounted at one end of the C-arm 40 via a support beam 46 and is oriented to direct a polychromatic x-ray fan beam 48 along beam axis 49 generally towards the isocenter 42 to a linear detector array 50 affixed to a stop plate 52 and mounted to the opposing end of the C-arm 40.

Together, motion of the pallet 34 and slider 36 permit a scanning by the detector 50 and radiation source 44 of the densitometer 10, whereas the motion of the turntable 39 allows for control of the angle of the beam axis 49 with respect to the patient 14, as will be described. The motion of the slider 36 is not limited to providing a scanning motion but may be used, in conjunction with rotation of the C-arm 40 in collar 38, to provide improved imaging of specific structures in the body without disturbing the patient 14 from the supine position. Referring to FIG. 6, imaging of the femur 53 of a supine patient 14 is ideally done at an angle of approximately 20°-25° from vertical. In prior art devices this typically required uncomfortable inward rotation of the leg of the patient 14. The ability, in the present invention, both to rotate the C-arm 40 and to move the slider 36 along the transverse axis 18, and thus to move the isocenter 42, permits this imaging to be done without movement of the patient 14. Specifically, the desired angle of the C-arm 40 is simply selected and the slider 36 moved so that the beam axis 49 aligns with the femur 53.

The use of a detector array 50 of individual detector elements, each element of which may be scanned to produce an attenuation reading of one ray of the fan beam 48, provides the densitometer 10 with the ability to scan at virtually any angle of the C-arm 40 largely independent of the limitations of the movement of the pallet 34 and slider 36 to a single plane. Scanning may be accomplished by selecting a primary scanning trajectory perpendicular to the fan beam axis 49 and calculating the protection of that trajectory on the plane of motion of the pallet 34 and slider 36 to determine the proper movement of the pallet 34 and the slider 36 that will produce motion of the C-arm 40 associated with that trajectory. As will be described below, the fan beam and the detector may then be rotated about the fan beam axis 49 so that the plane of the fan beam 48 is perpendicular to the trajectory to provide scanning, by scanning of the detector elements, in a second direction perpendicular to the primary scanning trajectory.

Alternatively, motion of the table 12 up and down combined with motion of the pallet 34 and slider 36 provides a set of three orthogonal motions that can be driven, under the control of computer 56, to produce any arbitrary primary scanning trajectory and a second perpendicular scanning motion according to basic trigonometric relations well understood to those of ordinary skill in the art.

Thus the present densitometer 10 allows scanned images to be obtained not simply along the anterior/posterior and lateral directions, but at any angle of the C-arm 40.

Each of these actions of the C-arm 40, the slider 36 and the pallet 34 may be controlled by a computer 56 having a display terminal 58 and a keyboard 60 such as are well known in the art. By providing step commands to the motors associated with the various components above described, the computer 56 may control and locate these components, for example, by adjusting and tracking the height of the table 12, through actuators 30. Similarly, the computer 56 may control the motion of the slider and gantry pallet 34 and 36, in producing a scan or in imaging the femur 53, the angular position of the C-arm 40, as well as movement of the support beam 46 as will be described. The computer 56 also turns the radiation source 44 on and off and importantly collects digitized attenuation data from the individual elements of the linear detector array 50 to generate an array of measured points (pixels) over the patient 14.

The linear detector array 50 may be a scintillation type detector, as is understood in the art, having scintillation materials which convert x-rays to visible light to be detected by photodetectors which produce a corresponding electrical signal. Each detector element 47 of the detector array 50 incorporates two side-by-side scintillators and photodetectors to measure the x-rays fluence, of the polychromatic fan beam 48, in one of two energy bands and thus to provide, during scanning, a dual energy measurement at each point in the scan. As noted above, such dual energy measurements allow the tissue of the patient 14 being measured at a given point associated with a detector element 47 to be characterized as to its composition, for example, into bone or soft tissue.

Figure 15:
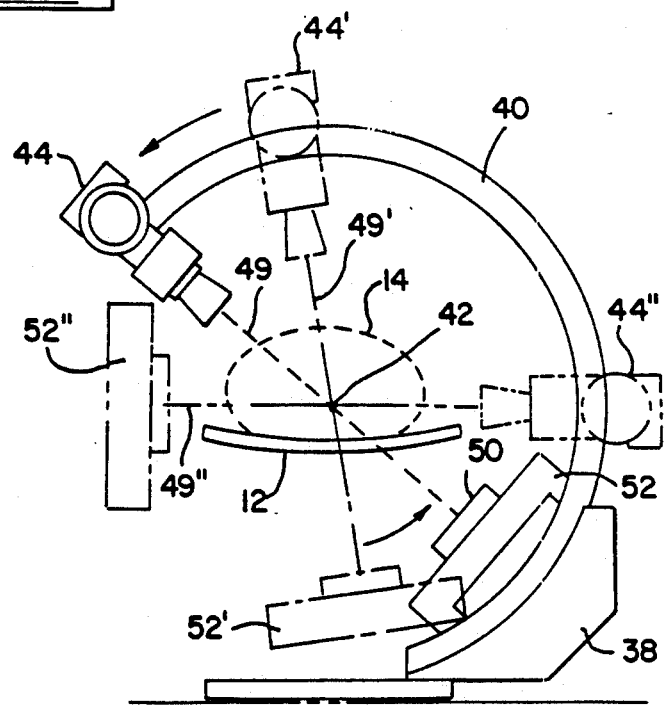
FIG. 15 is a schematic representation of motion of the C-arm showing the increased effective angular range obtained with the C-arm by motion of the radiation source and detector with respect to the C-arm itself.

Referring now to FIG. 15, the radiation source 44 and the detector array 50 may be positioned with respect to collar 38 so that the beam axis 49 is substantially horizontal to obtain a lateral scan of the patient 14 when the patient 14 is supine on the table 12. This lateral position is indicated by phantom radiation source 44'', beam axis 49'' and stop plate 52''. In the lateral position, the beam axis 49'' will intersect the isocenter 42. Referring also to FIG. 2(b), during this lateral scan, notches 24 may provide the table with a reduced profile in the critical spinal area to eliminate attenuation of the radiation fan beam 48 by the table 12.

By sliding the C-arm 40 through the collar 38, the radiation detector may be moved to a position indicated by phantom source 44' being angularly displaced from the position of phantom source 44'' by approximately 180° minus the angular extent of the collar 38. The stop plate 52 moves to the position shown by phantom stop plate 52' 180° opposed to phantom source 44'.

The angular extent of collar 38 prevents most C-arm system from realizing an angular range approaching 180° with motion of the C-arm 40 alone An additional angular range may be achieved in the present invention by extending the radiation source 44 on a support beam 46 and by sliding the stop plate 50 on a track formed in the C-arm 40 as shown in FIG. 5. The support beam 46 is generally arcuate with a radius $R_1$ in a first embodiment equal to the radius $R_2$ of the C-arm 40. This arcuate support beam 46 is supported by rollers 43 on a track 62 so as to telescope out of the end of the C-arm 40 and so as to move the radiation source 44 in an arc defined by radius $R_1$. The motion of the support beam 46 is accomplished by actuator 63 held within the C-arm 40 and attached between the inner most end of the support beam 46 and an internal portion of the C-arm 40 (not shown). The actuator 63 is driven by a stepper motor (not shown) so that it may operate under the control of computer 56, and so that smooth and controlled motion of the radiation source 44 may be obtained.

Figure 14:
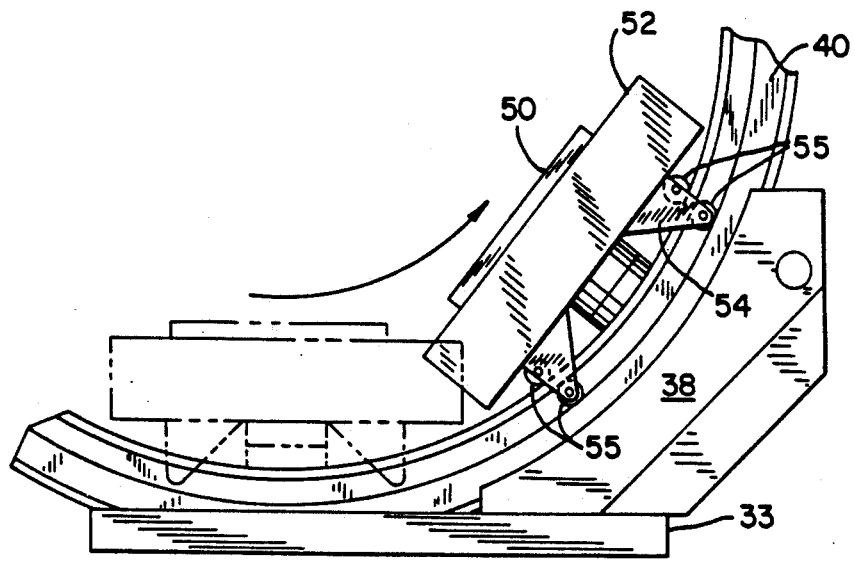
FIG. 14 is a detailed view in elevation of the detector of FIG. 1 showing the motion of the detector with respect to the C-arm

Referring also to FIG. 14, the stop plate 52 holding the detector 50 may be attached to a carriage 54 to slide on rollers 55 following a track formed in the inner surface of the C-arm 40. The track is positioned so that motion of the stop plate 52 is independent of position of the C-arm 40 within the collar 38, and so that the stop plate 52 may move with respect to the C-arm 40 past the collar 38 toward the position of the phantom source 44'. The motion of the stop plate 52 with respect to the C-arm 40 is controlled by the computer 56 via a stepper motor driven belt (not shown) according to methods understood to those of ordinary skill in the art.

Referring again to FIG. 15, the movement of the radiation source 44 past the end of the C-arm 40 and the motion of the stop plate 52 and detector 50 inward from the other end of the C-arm 40 allows an increase in the effective range of the angles of the beam axis 49 that may be obtained to substantially 180°.

Referring also to FIG. 5, in an alternative embodiment, the radius $R_2$ is not set equal to $R_1$. In particular, the radius $R_2$ of the C-arm 40 is the distance from the C-arm 40 to the isocenter 42. However, the radius $R_2$ of the support beam 46 is the distance between the radiation source 44 and the stop plate 52 or approximately twice that of $R_2$. Accordingly, with extension of the support beam 46, the radiation source 44 is moved so as to hold the beam axis 49 centered on the detector array 50 of the phantom stop plate 52' without movement of the stop plate 52'. In this embodiment, increased angular range may be obtained with movement only of the radiation source 44 with respect to the C-arm 40 but without movement of the detector 50 with respect to the C-arm 40.

It will be understood that in this latter embodiment, the extension of the support beam 46 increases the effective angular displacement of the radiation source 44 and detector array 50 at the cost of no longer maintaining isocentric motion about isocenter 42. The increase in effective angular rotation of the C-arm 40 will be equal to an angle $\alpha$ between the beam axis 49' of the radiation source 44' and the beam axis 49 of the radiation source 44 or approximately the length of the support beam 46 divided by $R_2$. This increase in the angular range achieved by C-arm 40 provides improved positioning flexibility for the densitometer 10.

As will be understood from this description, the same effective increase in the angular range of the C-arm 40 may be obtained by placing the detector array 50 on the support beam 46 and the radiation detector 44 on the carriage 54.

Referring now to FIG. 4, when the radiation source 44 and detector array 50 are oriented on the C-arm (not shown in FIG. 4) so that the beam axis 49 is substantially vertical, e.g. for anterior/posterior imaging, the table 12 may be lowered by a distance h to move the patient's spine 65 closer to the detector array 50 (indicated by 12') and in particular to decrease the distance between the spine 65 and the detector array 50. This movement of the spine 65 close to the detector array 50 reduces the effective magnification of the image 51 generated by the data from the detector array 50 by decreasing the angular dispersion of the rays of the x-rays fan beam 48 that intersect the spine 65. It will be understood that this use of the less divergent rays of the fan beam 48 reduces the effects of parallax in the produced image providing for more accurate imaging as is desirable for morphological measurements. Parallax as used herein refers to the variations in magnification between portions of the imaged anatomy, e.g. a vertebrae 64 of the spine 65, closer to and further away from the radiation source 44 such as may cause blurring int he image of the outline of the spine 65 detrimental to the identification of fiducial points within the spine 65. Large amounts of parallax, caused by diverging rays at large angles from the beam axis 49, cause blurring in edges of the bone that are substantially parallel to the beam axis 49, reducing the ability of the radiologist to locate the position of these edges precisely.

Control of the table height with positioning of the C-arm is performed by the computer 56 which has data indicating the position of each component of the densitometer 10 and which may calculate clearances between components at various positions by simple geometric calculations based on the dimensions of the components of the densitometer 10 as will be understood to those of ordinary skill in the art.

In order to move the C-arm 40 within collar 38 for repositioning, the table 12 is returned to a position removed from the linear detector array 50 and close to the isocenter 42 so as to permit unobstructed movement of the C-arm 40 without interference between the radiation source 44 and stop plate 52 with the table 12. Thus, the table motion accommodates the competing desires of: (1) keeping the radius of the C-arm 40 to a minimum to produce a compact densitometer 10 and to provide accurate morphological images in the anterior/posterior direction and (2) the desire to allow flexible repositioning without interference with the table 12.

Referring now to FIG. 7, the stop plate 52 is mounted on a rotating coupling 66 which may be driven by a stepper motor actuator (not shown) under the control of the computer 56 to rotate the stop plate 52, and hence the linear detector array 50, about the beam axis 49 by 90°. For repositioning movement of the C-arm 40, the stop plate 52 which serves to absorb scattered radiation from the radiation source 44, is rotated so that its longest dimension is generally tangential to the curve of the C-arm 40, reducing the swept volume of the stop plate 52 during rotation of the C-arm 40, from the swept volume indicted by 52', and allowing it to clear the table 12. The C-arm 40 is preferably positioned so that the path of the stop plate 52 passes through the notches 24 of the table 12. The combination of the notches 24 and the rotation of the stop plate 52 serves to further reduce the necessary radius of the C-arm 40 allowing a more compact densitometer 10 to be constructed.

Figure 8:
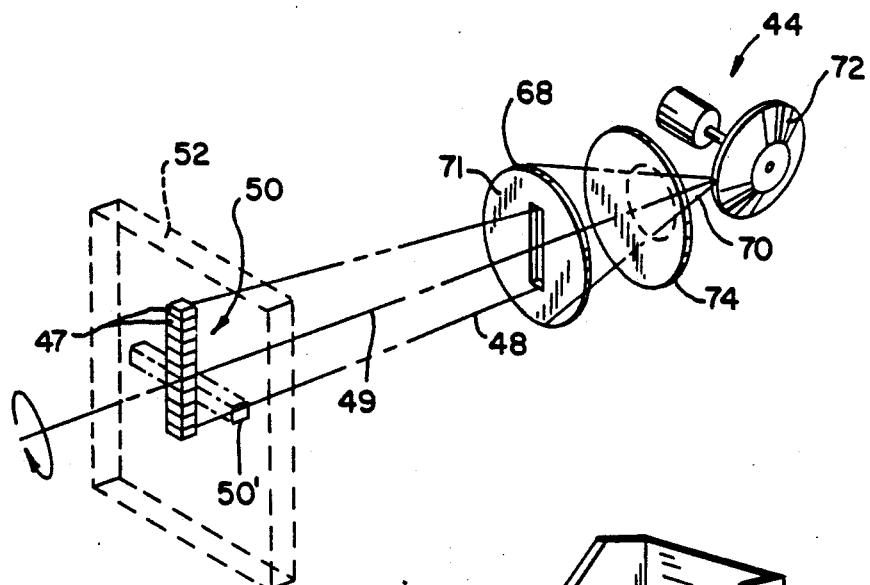
FIG. 8 is a exploded schematic view of the radiation source and a perspective view of the detector showing rotation of the fan beam by movement of a collimator and corresponding motion of the detector array.

Referring now to FIG. 8, the rotation of the stop plate 52 about the beam axis 49 to position the detector array 50 in one of two orientations, indicated by 50 and 50' respectively, may be matched by the rotation of the fan beam 48 from the radiation source 44. This rotation of the fan beam 48, which aligns the fan beam 48 with the length of the linear detector array 50, is preferably performed not by rotating the entire radiation source 44 but by rotating a slot collimator 68 to follow to the rotation of the stop plate 52. The slot collimator 68 incorporates a slot 71 defining the width and thickness of the fan beam 48 and which allows a passage of only a portion of a cone beam 70 generated by an anode 72 of an x-ray tube of the radiation source 44. The distribution of fluence within the cone beam 70 is typically not uniform and therefore a correcting wedge filter 74 is placed between the anode 72 and the slot collimator 68 so that in either rotative position of the slot collimator 68, a uniform distribution of energy is found within the fan beam 48.

It will be understood that the divergence of the fan beam 48 is greater in its width than in its thickness, and therefore, it is generally desirable for the purposes of morphological imaging to orient the fan beam 48, and the scanning direction, so that a fiducial plane of the imaged anatomy, e.g. the inferior or superior margins of vertebrae 64 are perpendicular to the scanning direction and generally parallel to the plane of the fan beam. For example, if the superior and inferior margins of a vertebrae 64 within the patient 14 are to be measured, it is desirable that the scanning direction be generally along the longitudinal axis 16 of the spine 65, with the plane of the fan beam 48 extending perpendicularly to the scanning direction i.e., transversely.

Referring now to FIG. 2(a), the ability to rotate the detector array 50 and thus to change the scanning direction allows tailoring the acquisition of attenuation data during a scan to minimize the potential for mis-registration between adjacent scan lines caused by movement of the patient 14. Assuming that the likelihood of patient motion between acquisition of data increases with time, this requirement devolves to a requirement that adjacent areas of the patient be scanned at times that are closely proximate to each other. For example, for a whole body scan of a patient 14, the detector array 50 could be oriented transversely as indicated by 50(b) so as to scan lines longitudinally as indicated generally by the sequence of areas A1, B1 and C1 from the patient's head to the patient's foot. At the end of this scan, a second longitudinal row of data would be taken conforming generally to the sequence of areas A2, B2 and C2. Under this scanning procedure, however, area A1 and B1 which are closely proximate, are separated by the considerable length of time required to scan the entire length of the patient 14. Preferably then, the detector array 50 may be positioned longitudinally as indicated by 50(a) to scan in columns by the sequence of A1, A2 and A3 and then B1, B2, B3. Here, the greatest motion induced discontinuity will be between area A1 and B1, however the length of time between the acquisition of data for these areas will have been much reduced.

Figure 10:
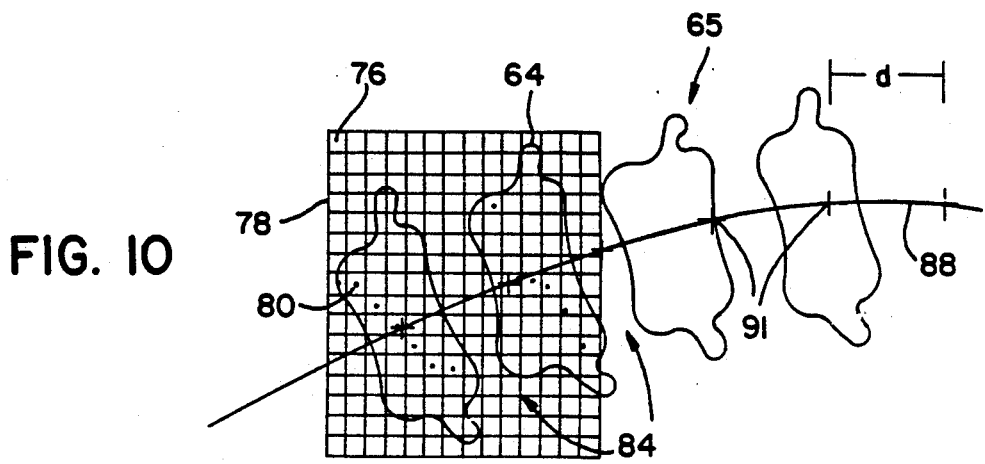
FIG. 10 is a detailed of a schematic, anterior/posterior view of the spine of a patient showing the resolution of the vertebrae into pixels for analysis.

Referring now to FIG. 10, in an anterior/posterior scan of the patient 14, where the beam axis 49 is oriented vertically, the data of a rectilinear array 78 of pixels 76 is acquired. Each pixel 76 of the array 78 has a location corresponding to a particular path of a ray of the fan beam 48 through the patient 14 to one detector element 47 of the detector array 50 and each pixel 76 having a value related to the attenuation of that ray as it passes through the patient 14. As is understood in the art, the computer 56 stores the pixel values and their relative spatial locations so that each pixel 76 may be readily identified to the particular area of the patient 14 at which the data of the pixel 76 was collected.

According to well understood dual energy imaging techniques, the value of each pixel 76 is derived from measurements of the patient at two energy levels and thus provides information indicating the composition of the material causing that attenuation. In particular, the pixel value indicates the bone mineral content of the volume of the patient corresponding to the pixel location.

Figures 11, 17:
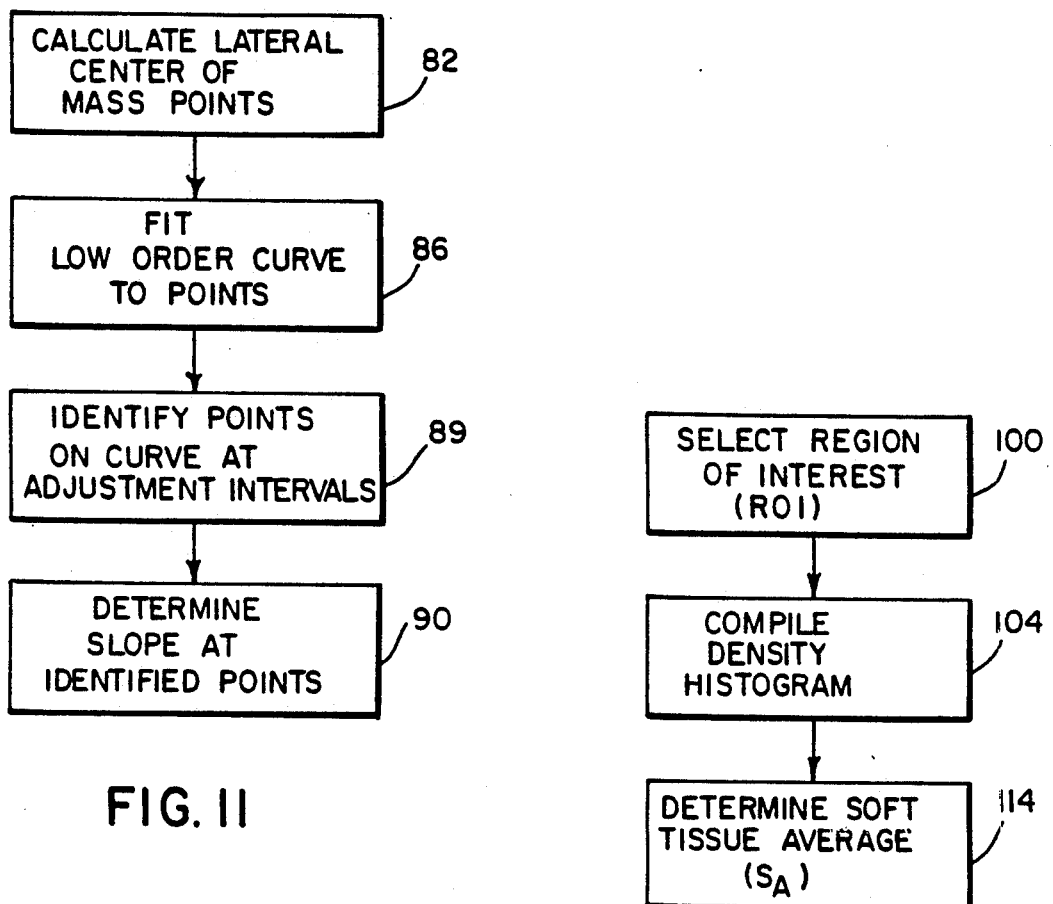
FIG. 11 is a flow chart illustrating the steps of determining the curvature of the spine of FIG. 10 in the lateral plane of the vertebrae of the patient such as may occur in scoliosis.
FIG. 17 is a flow chart showing a method for operation of the computer of FIG. 1 to identify and mask pixels attributable to osteophytes.

Referring to FIGS. 10 and 11, after collection of the pixels 76, the computer 56 determines a center of mass (value and location) 80 for each column of the array 78, as indicated by process block 82. A column is defined relative to the principle scanning direction. For a scan of the spine 65, where movement of the detector array 50 is longitudinal, i.e., along the superior/inferior direction 16 of the patient 14, the columns of pixels 76 are transverse or perpendicular to the scanning direction.

The center of mass 80 is simply an average of the location of each pixel 76 in the column weighted by the value of the pixel 76, and thus generally indicates the center of the bone mass within that column.

The calculation of center of mass points 80 is performed by computer 56 and repeated for each column of pixel data within the array 78 to provide a general indication of the degree of lateral curvature of the patient's as evident in the anterior/posterior view. Although bone other than the spine 65 may be included within the field of view covered by the array 78, such bone, such as from the ribs, will generally cancel out in the center of mass calculation as a result of the fundamental bi-lateral symmetry of the patient 14.

In areas of low bone mass, such as intervertebral areas 84, spurious center of mass values may be obtained as a result of lack of significant bone mineral content. Accordingly, implicit in process block 82, is the elimination of calculated center of mass points 80 having a value (as opposed to location) below of predetermined threshold.

Figure 12:
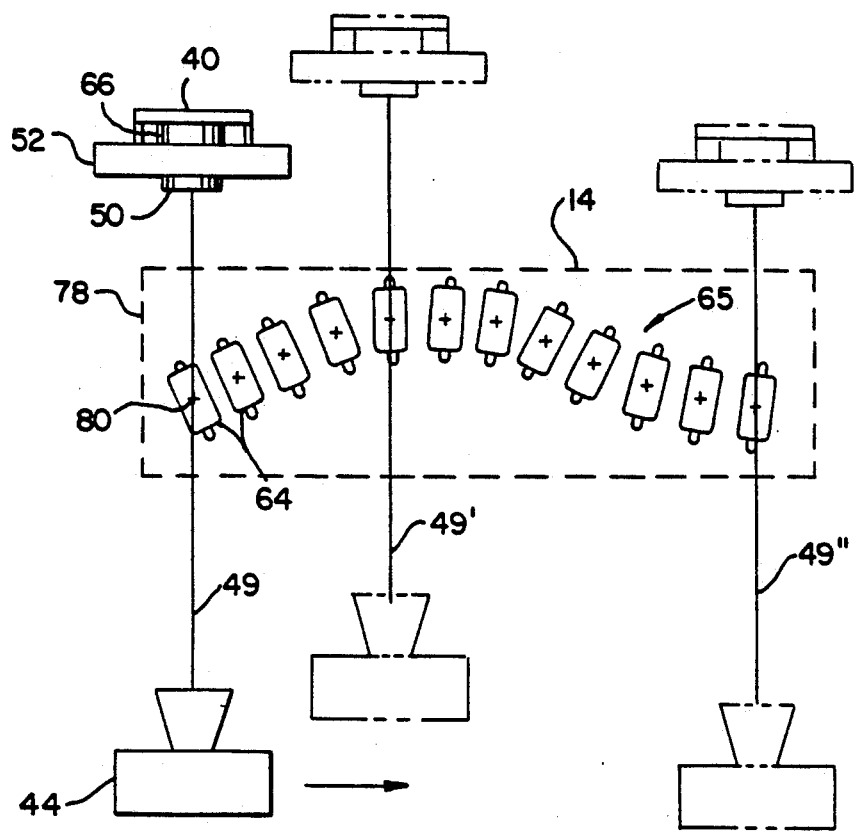
FIG. 12 is a schematic, plan view showing the movement of the x-ray source and the detector of FIG. 1 to follow the curvature of the spine in lateral imaging, per the density measuring view of FIG. 10, according to a first embodiment.

In one embodiment, illustrated in FIG. 12, the center of mass points 80 guide the positioning of the detector 50 and the radiation source 44 during a lateral scanning of the patient 14. The lateral scan is generally employed in the morphologic analysis of the vertebrae 64 and thus precise control of the magnification of the produced image is important. During the lateral scan, the center of mass points 80 of the array 78, as related to actual positions within the patient 14, are used to control the distance between the detector array 50 and the patient 14 so that the distance between the center of mass point 80 (intersected by the beam axis 49) and the detector array 50 is held substantially constant during the scan. The effect of this is that the magnification of an individual vertebra 64 in the produced image will remain substantially constant despite severe curvature or scoliosis of the spine 65 of the patient 14.

This lateral correcting movement of the detector 50 with respect to the patient 14 during the scan is provided by motion of the slider 36 (shown in FIG. 9) under control of the computer 56 as has been described. The principle motion of the scanning, in this example, is provided by motion of the pallet 34 along rails 32.

As the scan progresses, if there is no center of mass point 80 intersected by beam axis 49, the relative transverse location of the detector 50 is simply held constant. Alternatively, the position of the center of mass points 80 may be interpolated to obtain precise tracking of the detector 50 between center of mass points, such as in the intervertebral areas 84.

In this example, the anterior/posterior view is used to provide more accurate imaging in the lateral view by indicating relative lateral displacement of the imaged structure. It will recognized, however, that the above described technique is not limited to use with anterior and lateral projections but may be employed with images obtained at any two gantry angles having sufficient separation to provide the necessary third dimensions of information. Corrective motion during the second scan may be obtained by movement of various other axes of the densitometer system including vertical motion of the table 12 as has been previously described. Specifically, motion of the table may be used to provide corrected imaging of spinal curvature apparent in a lateral scan.

Referring again to FIGS. 10 and 11, improved correction of the important lateral image may be obtained by fitting a low order curve 88 to the center of mass points 80 as indicated by process block 86. This low order curve 88 provides a more accurate modeling of the curvature of the spine 65 that is not perturbed by local variations in bone density within a given vertebra 64. The low curve 88 may be a simple third order polynomial fitted by least squares techniques applied by computer 56 as is well understood in the art.

After fitting of this curve 88 to the center of mass points 80, a set of scan points 91, equally spaced by d along the curve 88, may be identified according to process block 89 and the slope $\theta$ of the curve 88 at those points 91 determined by numerical differentiation according to process block 90. Typically, these scan points are separated by the pixel to pixel spacing and are shown with exaggerated spacing in FIG. 10 for clarity. These slope values $\theta_i$ where i is the index of the particular scan point 91 on the curve 88, may be used to control the angle $\theta$ at which the beam axis 49 is tipped with respect to the scan direction 16 so that the beam axis 49 intersects the imaged vertebra 64 at nearly 90° to the spine axis, thus providing a sharper imaging of the laterally extending fiducial edges of the vertebra that are diagnostically significant.

Figure 13:
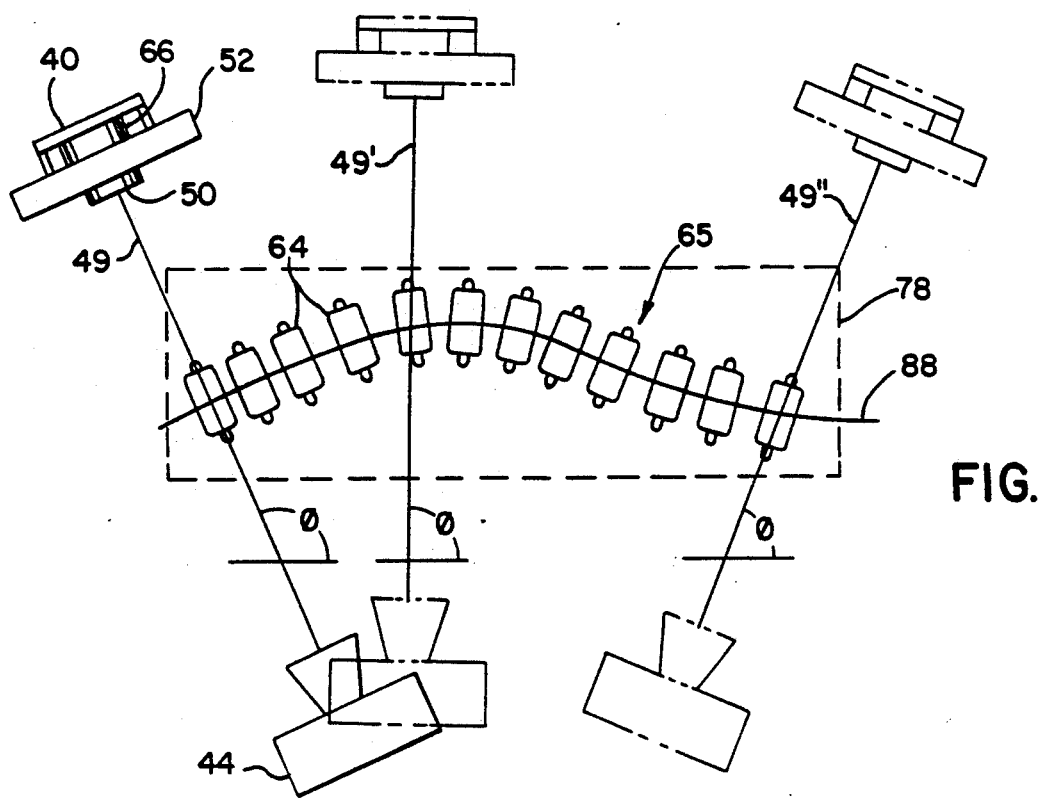
FIG. 13 is a schematic, plan view showing the movement of the x-ray source and the detector of FIG. 1 to follow the curvature of the spine in lateral imaging, per the density measuring view of FIG. 10, according to a second embodiment.

Referring now to FIG. 13, the angle of the beam axis $\theta$ with respect to the principal axis of scanning 16 is controlled during the scanning along the principle axis of scanning by tilting of the detector array 50 and radiation source 44 on C-arm 40 by means of motion of turntable 39 (of FIG. 9) under the control of computer 56. Pixel data is acquired as the radiation axis 49 crosses each of the predefined scan points 91.

Referring again to FIG. 10 certain pixels 76 of the array 78 may be identified to a region of interest (ROI) over which an average bone density value (mass per area) may be developed. Such bone density measurements are useful in evaluating the health of the bone and in tracking bone mineral loss in diseases such as osteoporosis.

Measurements of average bone density in the ROI may be distorted by the inclusion of very dense, non-bone elements such as metal pins and the like. The density of metal is much greater than that of bone and biases the average density reading upward, rendering it less accurate. Typically, the influence of metallic elements within the ROI is eliminated from the average density measurement by a simple thresholding process in which pixels having a density value greater than a fixed value are ignored in the calculation of the average.

The present invention has recognized that the average bone density value within the ROI may also be distorted by the presence of osteophytes which have a density higher than that of bone but not so high so that they can be easily separated from bone by a simple thresholding process.

Figure 16:
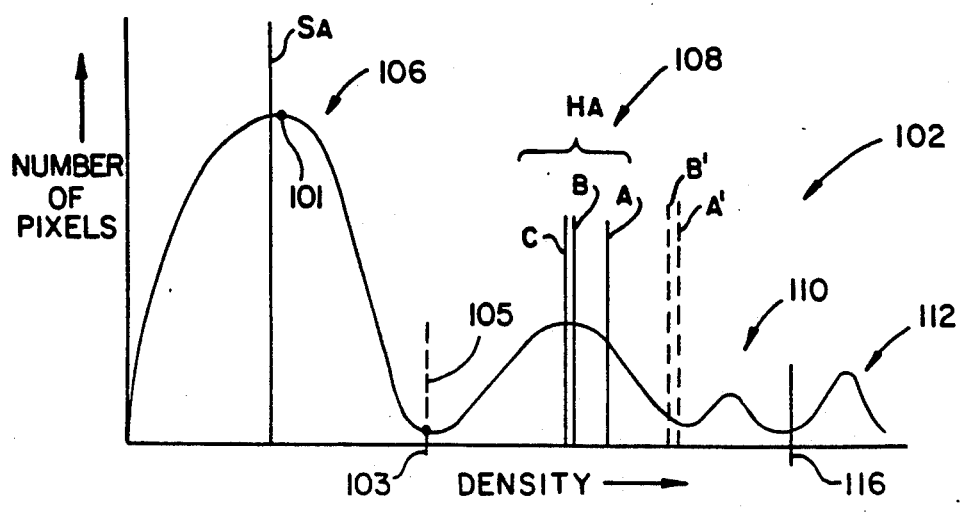
FIG. 16 is a simplified histogram of the density of pixels within a region of interest of a patient showing the concentration of pixels into four density ranges or modes of: soft tissue, hard tissue (bone), osteophytes, and metal.

Referring to FIG. 16 and 17, once a region of interest of pixels 76 has been selected as indicated by process block 100, the particular pixel values are analyzed by the computer 56 to compile a density histogram 102 as indicated by process block 104. The density histogram plots on the horizontal axis, possible density values of each pixel 76 and on a vertical axis, the number of pixels 76 having a given density value. A typical histogram 102 will include groupings of pixels having similar density values. Such groupings will be termed "modes".

A first mode 106 includes pixels 76 of low density associated with soft tissue, and a second mode 108 includes pixels 76 of higher density 108 associated with bone, Generally, the first and second modes 106 and 108 are separated by a readily determined threshold value 105. A third mode 110 consists of pixels 76 of yet higher density of a range associated with osteophytes. This third mode 110 is shown for illustration clearly separated from the second mode 108 but in practice the separation is ill-defined. Finally, a fourth mode 112 of pixels 76 may exist being of even higher density than modes 106, 108 and 110 and associated with pixels measuring metallic pins and the like. The density of the metals is so much greater than that of the pixels of modes 106, 108, and 110 that a metal threshold 116 may be established a priori to distinguish this mode 112 from the others.

As mentioned, the soft tissue mode 106 may be readily distinguished from the other modes 108-112 and isolated by identifying the first local maxima 101 and first local minima 103 after that maxima 101. This minima 103 becomes the value of the threshold 105.

At process block 114, an average density of the soft tissue pixels 106 is determined as designated $S_A$. As will be recognized to those of ordinary skill in the art, this average will simply be the center of mass of the lobe of mode 106 of the histogram 102.

At process block 118, an average density value for hard tissue ($H_A$) is determined by evaluating all those pixels not within the group 106, e.g., above threshold 105 and below the metal threshold 116. This value, $H_A$, will include certain pixels within mode 110 of the osteophytes and is indicated by line A on the histogram 102 of FIG. 16.

At decision block 120, the value of $H_A$ is compared to a previously computed value of $H_A$, if any. For the first iteration, there will be no previously computed value of $H_A$ and the program will proceed to process block 122 at which a threshold is established designated A' in FIG. 16 and being equal to the currently computed average density value of hard tissue plus 20% of the deference between the average value of the hard tissue minus the average value in density of the soft tissue or:

$$H_A + 0.2(H_A - S_A) \tag{1}$$

With this threshold in place the program proceeds again to process block 118 and a new average density value for hard tissue is established, generally lower than the previous average value and indicated by line B of FIG. 16, and which ignores those pixels above the threshold A'. Typically this new value of $H_A$ will be significantly different from the previous $H_A$, i.e., by more than the predetermined threshold of decision block 120, and therefore the program loops back to process block 122 and a new threshold B' is computed ordinarily of a lower density value than A'.

This process is repeated until the newly computed value of $H_A$ converges to within the predetermined threshold of decision block 120 of the immediately preceding value of $H_A$. At this time, decision block 120 within the loop formed by process blocks 118 and 122, directs the program to process block 124 and the value of $H_A$ last computed is adopted as the bone mineral content value for the ROI. The final threshold established by line C' and implicit in the masking calculation of process block 122 may be used to generate an image of bone with the osteophytes removed per process block 126.

In a further embodiment, those masked pixels of group 110 may be analyzed as to their spatial locations and isolated pixels, i.e., those not having neighboring pixels within group 110 may be unmasked reflecting the rule that the osteophytes are typically of a size that spans at least two pixels of the image.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. A method of making measurements of vertebrae of a patient's spine with a densitometer having an opposed radiation source and detector, the source and detector moving to a first and second angle about the spine and at each angle scanning to obtain a two dimensional array of pixels representing the attenuation of radiation at corresponding locations through the patient, comprising the steps of:
    positioning the source and detector at the first angle and scanning the vertebrae along a first axis to obtain the first array of pixels;
    analyzing the first array of pixels to determine center of bone mass values at a plurality of points along an axis of the array corresponding to the first axis;
    positioning the source and detector at a second angle substantially perpendicular to the first angle;
    scanning along the first axis of the patient to obtain the second array of pixels;
    adjusting the position of the detector with respect to the patient during the scanning at the second angle in accordance with the determined center of bone mass values of the first array of pixels.

2. The method of claim 1 wherein the step of adjusting the position of the detector adjusts the distance of the detector from the patient so as to render the distance between the detector and the center of bone mass, as intersected by a line between the source and detector, substantially constant during the scanning at the second angle.

3. The method of claim 1 including the additional steps of:
    disregarding those center of bone mass values for points along the axis of the array where the center of mass values are below a predetermined threshold; and
    fitting a curve to the remaining plurality of center of bone mass values and employing points on the curve as the center of bone mass values.

4. The method of claim 3 including the step of determining the slope of the curve to produce a set of slope values; and
    wherein the step of adjusting the position of the detector adjusts the angle of a line between the source and detector so that the intersection of the line and the curve as superimposed on the patient is at an angle so that the line and curve are substantially perpendicular at the intersection.

5. A method of identifying osteophytes in a bone density image comprising the steps of:
    (a) employing a bone densitometer to obtain a plurality of pixels each having a density value and a spatial location;
    (b) determining a region of interest comprising selected pixels of the image;
    (c) reviewing the selected pixels to create a multiple mode density histogram providing frequency of density values of pixels as a function of density value;
    (d) identifying the lowest density mode to produce a soft tissue average $S_A$;
    (e) identifying a second lowest density mode of pixels not in the lowest density mode to produce a hard tissue average $H_A$;
    (f) establishing a threshold above the hard tissue average based on the difference between the hard tissue average and the soft tissue average;
    (g) recomputing the hard tissue average ignoring pixels above the threshold;
    (h) repeating steps (a) through (f) until the change in the computed hard tissue average is below a predetermined threshold; and
    (i) displaying the current hard tissue average.

* * * * *